US00PP32240P2

(12) United States Plant Patent
Arts

(10) Patent No.: US PP32,240 P2
(45) Date of Patent: Sep. 29, 2020

(54) ***HYDRANGEA* PLANT NAMED 'H218923'**

(50) Latin Name: *Hydrangea macrophylla*
Varietal Denomination: H218923

(71) Applicant: HYDRANGEA BREEDERS ASSOCIATION B.V., De Kwakel (NL)

(72) Inventor: Niels Arts, Aalsmeer (NL)

(73) Assignee: Hydrangea Breeders Association B.V., De Kwakel (NL)

( * ) Notice: Subject to any disclaimer, the term of this patent is extended or adjusted under 35 U.S.C. 154(b) by 0 days.

(21) Appl. No.: 16/602,113

(22) Filed: Aug. 7, 2019

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
CPC ... A01H 5/02; A01H 5/00; A01H 6/48; A01H 1/02
See application file for complete search history.

*Primary Examiner* — June Hwu
(74) *Attorney, Agent, or Firm* — C. A. Whealy

(57) ABSTRACT

A new and distinct cultivar of *Hydrangea* plant named 'H218923', characterized by its upright and uniformly mounded plant habit; vigorous growth habit and rapid growth rate; freely branching habit with strong, thick and sturdy stems; freely and uniformly flowering habit; mop-head-type inflorescences with numerous white to very light red purple-colored sterile flowers; and good postproduction longevity.

3 Drawing Sheets

Botanical designation: *Hydrangea macrophylla.*
Cultivar denomination: 'H218923'.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'H218923'.

The new *Hydrangea* plant is a product of a planned breeding program conducted by the Inventor in De Kwakel, The Netherlands and Lengerich, Germany. The objective of the breeding program was to create new strong and freely-branching *Hydrangea* plants with strong sturdy stems, uniform flowering habit, large inflorescences with numerous showy sterile flowers, attractive sterile flower color and good postproduction longevity.

The new *Hydrangea* plant originated from a cross-pollination made by the Inventor in March, 2014 in De Kwakel, The Netherlands, of *Hydrangea macrophylla* 'Saxdifioros', disclosed in U.S. Plant Pat. No. 28,838, as the female, or seed, parent with *Hydrangea macrophylla* 'Preziosa', not patented, as the male, or pollen, parent. The new *Hydrangea* plant was discovered and selected by the Inventor as a single flowering plant from within the progeny of the stated cross-pollination in a controlled greenhouse environment in Lengerich, Germany in March, 2015.

Asexual reproduction of the new *Hydrangea* plant by vegetative tip cuttings in a controlled environment in De Kwakel, The Netherlands since April, 2016 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'H218923'. These characteristics in combination distinguish 'H218923' as a new and distinct *Hydrangea* plant:

1. Upright and uniformly mounded plant habit.
2. Vigorous growth habit and rapid growth rate.
3. Freely branching habit with strong, thick and sturdy stems.
4. Freely and uniformly flowering habit.
5. Mophead-type inflorescences with numerous white to very light red purple-colored sterile flowers.
6. Good postproduction longevity.

Plants of the new *Hydrangea* can be compared to plants of the female parent, 'Saxdifioros'. Plants of the new *Hydrangea* differ primarily from plants of 'Saxdifioros' in sterile flower color as plants of the new *Hydrangea* have white to very light red purple-colored sterile flowers whereas plants of 'Saxdifioros' have bright pink-colored sterile flowers.

Plants of the new *Hydrangea* can be compared to plants of the male parent, 'Preziosa'. Plants of the new *Hydrangea* differ primarily from plants of 'Preziosa' in sterile flower color as plants of the new *Hydrangea* have white to very light red purple-colored sterile flowers whereas plants of 'Preziosa' have light pink-colored sterile flowers with dark pink-colored margins.

Plants of the new *Hydrangea* can be compared to plants of the *Hydrangea macrophylla* 'Agrihydravijf', disclosed in U.S. Plant Pat. No. 19,731. In side-by-side comparisons, plants of the new *Hydrangea* differ primarily from plants of 'Agrihydravijf' in the following characteristics:

1. Plants of the new *Hydrangea* are taller than plants of 'Agrihydravijf'.
2. Plants of the new *Hydrangea* have smaller panicles than plants of 'Agrihydravijf'.
3. Plants of the new *Hydrangea* have white to very light red purple-colored sterile flowers whereas plants of 'Agrihydravijf' have light pink-colored sterile flowers.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet is a side perspective view of a typical flowering plant of 'H218923'.

The photograph on the second sheet is a close-up view of a typical inflorescence of 'H218923'.

The photograph on the third sheet is a top perspective view of a typical flowering plant of 'H218923' that has been "blued" (left) that is, treated with aluminum sulfate, and a top perspective view of a typical flowering plant of 'H218923' that has not been "blued" (right) that is, not treated with aluminum sulfate.

DETAILED BOTANICAL DESCRIPTION

Plants used in the aforementioned photographs and in the following description were grown during the late spring and early summer in 13-cm containers in a glass-covered greenhouse in De Kwakel, The Netherlands and under cultural practices typical of commercial *Hydrangea* production. During the production of the plants, day and night temperatures averaged 17° C. Plants of the new *Hydrangea* were one year old when the photographs and description were taken. Plants of the new *Hydrangea* can be treated with aluminum sulfate to "blue" the inflorescences, however, the effect is slight and is typically not done commercially. In the following description, color references are made to The Royal Horticultural Society Colour Chart, 2015 Edition, except where general terms of ordinary dictionary significance are used.

Botanical description: *Hydrangea macrophylla* 'H218923'.

Parentage:

*Female, or seed, parent.*—*Hydrangea macrophylla* 'Saxdifioros', disclosed in U.S. Plant Pat. No. 28,838.

*Male, or pollen, parent.*—*Hydrangea macrophylla* 'Preziosa', not patented.

Propagation:

*Type cutting.*—By vegetative tip cuttings.

*Time to initiate roots, summer.*—About two weeks at temperatures about 23° C.

*Time to initiate roots, winter.*—About 18 days at temperatures about 20° C.

*Time to produce a rooted young plant, summer.*—About four weeks at temperatures about 23° C.

*Time to produce a rooted young plant, winter.*—About five weeks at temperatures about 20° C.

*Root description.*—Thick; typically whitish brown in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Upright and uniformly mounded plant habit; strong and sturdy stems; rapid growth rate and vigorous growth habit.

*Plant height.*—About 25 cm to 35 cm.

*Plant diameter or area of spread.*—About 55 cm.

Lateral branch description:

*Branching habit.*—Freely branching habit; when pinched, about twelve lateral branches develop per plant.

*Length.*—About 25 cm to 30 cm.

*Diameter.*—About 4 mm to 5 mm.

*Internode length.*—About 6 cm to 8 cm.

*Texture.*—Smooth, glabrous; fully developed, woody.

*Aspect.*—Upright to about 20° from vertical.

*Strength.*—Strong, sturdy.

*Color.*—When developing: Close to 145A; at internodes, close to 145A; lenticels, close to 187B. Developed: Close to 145A; at the internodes, close to 187A; when woody, close to 177C; lenticels, close to 187B.

Leaf description:

*Arrangement.*—Opposite, simple.

*Length.*—About 11 cm to 13 cm.

*Width.*—About 6 cm to 7 cm.

*Shape.*—Ovate to lanceolate.

*Apex.*—Acute.

*Base.*—Attenuate.

*Margin.*—Dentate to serrate.

*Texture, upper surface.*—Smooth to rugose, glabrous.

*Texture, lower surface.*—Rugose, glabrous.

*Venation pattern.*—Pinnate.

*Color.*—Developing leaves, upper surface: Close to 144C. Developing leaves, lower surface: Close to 137D. Fully expanded leaves, upper surface: Close to 137A; venation, close to 145B. Fully expanded leaves, lower surface: Close to 137C; venation, close to 145D.

*Petioles.*—Length: About 2 cm to 2.5 cm. Diameter: About 3 mm to 4 mm. Texture, upper and lower surfaces: Smooth, glabrous. Color, upper surface: Close to 145B. Color, lower surface: Close to 145D.

Flower description:

*Flower type and habit.*—Showy sterile flowers and small inconspicuous fertile flowers arranged on mophead-type terminal panicles; panicles globular in shape; flowers face upright to outwardly depending on their position in the inflorescence.

*Fragrance.*—None detected.

*Natural flowering season.*—Plants begin flowering about one year after planting; flowering begins in the early summer and is continuous throughout the summer in Northern Europe.

*Flower longevity.*—Fertile flowers last about one month on the plant, fertile flowers not persistent; sterile flowers last about four months on the plant, sterile flowers persistent.

*Quantity of flowers.*—Freely flowering habit; about 50 to 60 fertile flowers per panicle and about 80 to 100 sterile flowers per panicle.

*Panicle height.*—About 6 cm to 8 cm.

*Panicle diameter.*—About 9 cm to 12 cm.

*Fertile flower buds*.—Length: About 3 mm. Diameter: About 3 mm. Shape: Spherical. Color: Close to 75C.

*Sterile flower buds*.—Length: About 3 mm. Diameter: About 3 mm. Shape: Spherical. Color: Close to 144B.

*Fertile flower diameter*.—About 3 mm.

*Fertile flower depth* (*height*).—About 3 mm.

*Sterile flower diameter*.—About 3.5 cm to 4 cm.

*Sterile flower depth* (*height*).—About 1 cm.

*Petals, fertile flowers*.—Quantity and arrangement: Four or five in a single whorl. Length: About 3 mm. Width: About 2 mm. Shape: Ovate. Apex: Acute. Base: Attenuate. Margin: Entire. Texture, upper and lower surfaces: Smooth, glabrous. Color: When opening, upper and lower surfaces: Close to 145D. Fully opened, upper and lower surfaces: Close to 75C; color does not change with development.

*Petals, sterile flowers*.—Quantity and arrangement: Three or four in a single whorl. Length: About 3 mm. Width: About 2 mm. Shape: Ovate. Apex: Acute. Base: Obtuse. Margin: Entire. Texture, upper and lower surfaces: Smooth, glabrous. Color: When opening, upper and lower surfaces: Close to 145C. Fully opened, upper and lower surfaces: Close to 75B; color does not change with development.

*Sepals, fertile flowers*.—Quantity and arrangement: Five in a single whorl. Length: About 2.5 mm. Width: About 1.5 mm. Shape: Ovate. Apex: Acute. Base: Obtuse. Margin: Entire. Texture, upper and lower surfaces: Smooth, glabrous. Color: When opening, upper surface: Close to 145D. When opening, lower surface: Close to 145C. Fully opened, upper and lower surfaces: Close to 69D; color does not change with development.

*Sepals, sterile flowers*.—Quantity and arrangement: Three or four in a single whorl. Length: About 1.5 cm to 2 cm. Width: About 2 cm to 2.5 cm. Shape: Deltoid. Apex: Obtuse. Base: Cuneate. Margin: Entire. Texture, upper and lower surfaces: Smooth, glabrous. Color: When opening, upper and lower surfaces: Close to 145C becoming closer to 157D with development. Fully opened, upper surface: Close to NN155D becoming closer to 69D with development; with subsequent development, color becoming closer to 69D and 145B; when "blued", becoming closer to N155A and 91D. Fully opened, lower surface: Close to NN155D becoming closer to 69D with development; with subsequent development, color becoming closer to 69D and 145D.

*Pedicels, fertile flowers*.—Length: About 3 mm to 5 mm. Diameter: About 1 mm. Strength: Strong. Aspect: Mostly upright. Texture: Smooth, glabrous. Color: Close to 69D.

*Pedicels, sterile flowers*.—Length: About 2 cm to 2.5 cm. Diameter: About 2 mm to 3 mm. Strength: Strong. Aspect: Erect to about 45° from vertical. Texture: Smooth, glabrous. Color: Close to 69B.

*Reproductive organs, fertile flowers*.—Stamens: Quantity per flower: Eight. Filament length: About 1 mm. Filament color: Close to 70C. Anther length: About 1 mm. Anther shape: Conical. Anther color: Close to 75B. Pollen amount: Abundant. Pollen color: Close to 155D. Pistils: Pistil quantity per flower: Three. Pistil length: About 3 mm. Stigma shape: Oval. Stigma color: Close to 75C. Style length: About 1 mm. Style color: Close to N74D. Ovary color: Close to N74D.

*Reproductive organs, sterile flowers*.—To date, stamen and pistil development has not been observed on plants of the new *Hydrangea*.

*Seeds, only produced by fertile flowers*.—Quantity per fertile flower: About 20 to 30. Length: About 0.5 mm. Diameter: About 0.1 mm. Color: Close to 200C.

Pathogen & pest resistance: Under commercial production conditions, plants of the new *Hydrangea* have not been observed to be resistant to pathogens and pests common to *Hydrangea* plants to date.

Temperature tolerance: Plants of the new *Hydrangea* have been shown to be tolerant to temperatures ranging from about 3° C. to about 38° C.

It is claimed:

1. A new and distinct *Hydrangea* plant named 'H218923' as illustrated and described.

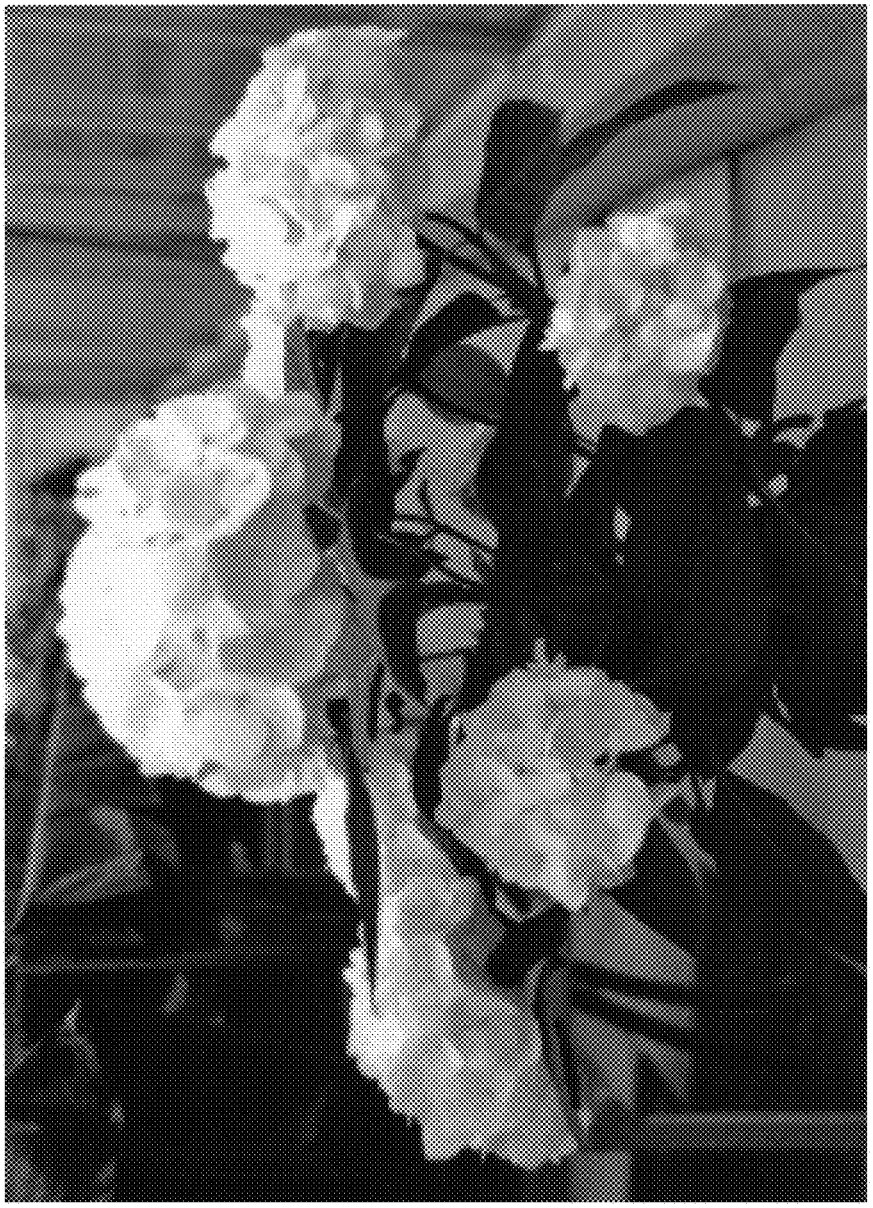

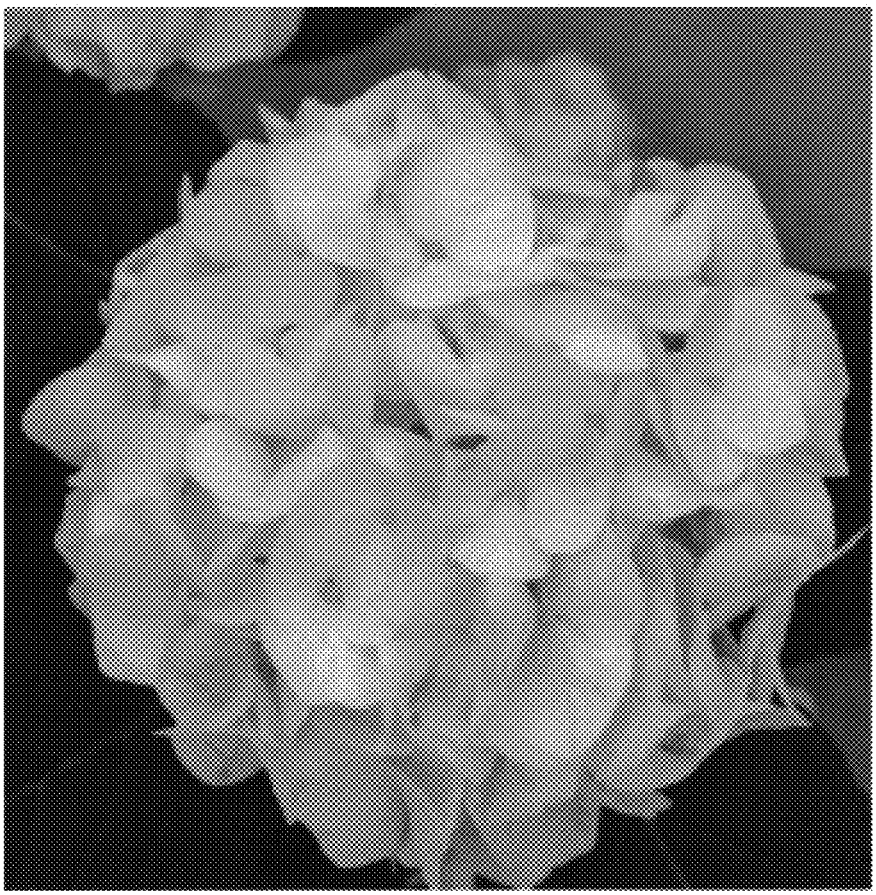

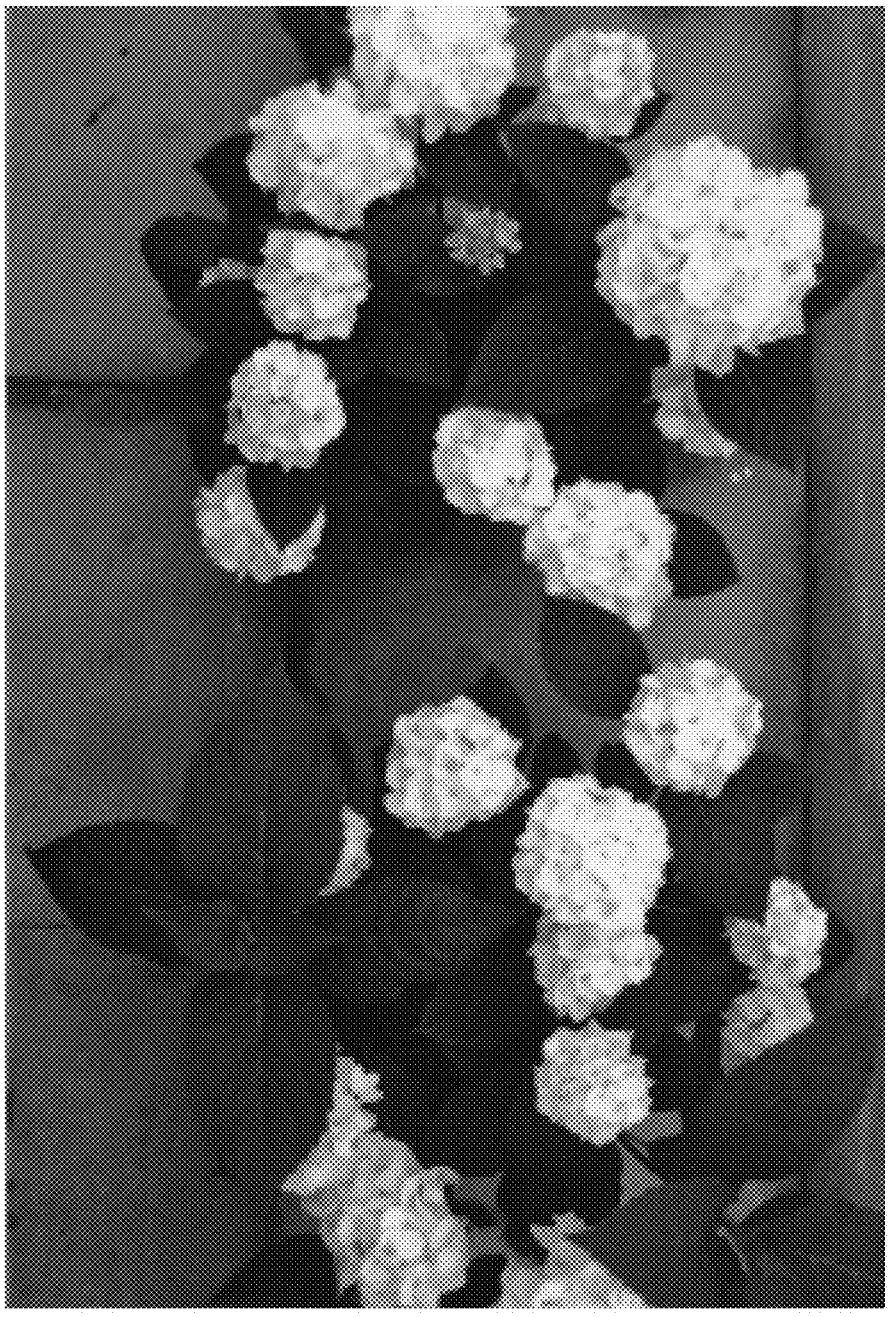

* * * * *